US011589933B2

(12) United States Patent
Esterberg et al.

(10) Patent No.: US 11,589,933 B2
(45) Date of Patent: Feb. 28, 2023

(54) GUIDING A ROBOTIC SURGICAL SYSTEM TO PERFORM A SURGICAL PROCEDURE

(71) Applicant: IX Innovation LLC, Seattle, WA (US)

(72) Inventors: Justin Esterberg, Mercer Island, WA (US); Jeffrey Roh, Seattle, WA (US)

(73) Assignee: IX INNOVATION LLC, Seattle, WA (US)

( * ) Notice: Subject to any disclaimer, the term of this patent is extended or adjusted under 35 U.S.C. 154(b) by 757 days.

(21) Appl. No.: 16/023,014

(22) Filed: Jun. 29, 2018

(65) Prior Publication Data
US 2019/0000570 A1    Jan. 3, 2019

Related U.S. Application Data

(60) Provisional application No. 62/526,439, filed on Jun. 29, 2017, provisional application No. 62/528,102, filed on Jul. 2, 2017, provisional application No. 62/529,019, filed on Jul. 6, 2017.

(51) Int. Cl.
| | |
|---|---|
| *A61B 34/30* | (2016.01) |
| *A61B 90/00* | (2016.01) |
| *A61B 17/16* | (2006.01) |
| *A61B 34/20* | (2016.01) |
| *A61B 34/00* | (2016.01) |
| *A61B 17/00* | (2006.01) |
| *A61B 34/10* | (2016.01) |
| *A61B 90/50* | (2016.01) |

(52) U.S. Cl.
CPC .......... *A61B 34/30* (2016.02); *A61B 17/1615* (2013.01); *A61B 34/20* (2016.02); *A61B 90/361* (2016.02); *A61B 90/37* (2016.02); *A61B 17/00234* (2013.01); *A61B 17/1622* (2013.01); *A61B 34/74* (2016.02); *A61B 2034/102* (2016.02); *A61B 2034/105* (2016.02); *A61B 2034/107* (2016.02); *A61B 2034/2048* (2016.02); *A61B 2034/256* (2016.02); *A61B 2034/305* (2016.02); *A61B 2090/365* (2016.02); *A61B 2090/371* (2016.02); *A61B 2090/372* (2016.02); *A61B 2090/3937* (2016.02); *A61B 2090/502* (2016.02)

(58) Field of Classification Search
None
See application file for complete search history.

(56) References Cited

U.S. PATENT DOCUMENTS

| | | | |
|---|---|---|---|
| 9,469,034 B2* | 10/2016 | Diolaiti | A61B 34/72 |
| 2003/0179308 A1* | 9/2003 | Zamorano | A61B 5/00 |
| | | | 348/333.12 |

(Continued)

*Primary Examiner* — Katherine L Fernandez
(74) *Attorney, Agent, or Firm* — Hamre, Schumann, Mueller & Larson, P.C.

(57) ABSTRACT

A robotic surgical system may be used to perform a surgical procedure. Providing guidance for the robotic surgical system includes integrating a Point of View (PoV) surgical drill with a camera to capture a PoV image of a surgical area of a subject patient; displaying an image of the surgical area, based on a viewing angle of the PoV surgical drill, thus enabling the surgeon to operate on the surgical area using the PoV surgical drill. The PoV surgical drill operates based on the surgeon's control of a guidance drill. The content of the images may change based on a change in the viewing angle of the PoV surgical drill.

15 Claims, 5 Drawing Sheets

(56) References Cited

U.S. PATENT DOCUMENTS

| | | | |
|---|---|---|---|
| 2011/0238079 A1* | 9/2011 | Hannaford | A61B 34/35 |
| | | | 606/130 |
| 2014/0232824 A1* | 8/2014 | DiMaio | A61B 34/30 |
| | | | 348/45 |
| 2014/0236159 A1* | 8/2014 | Haider | A61B 17/1626 |
| | | | 606/88 |
| 2017/0135776 A1* | 5/2017 | Cohen | B25J 9/0084 |
| 2018/0071032 A1* | 3/2018 | de Almeida Barreto | |
| | | | A61B 34/10 |

* cited by examiner

GUIDING A ROBOTIC SURGICAL SYSTEM TO PERFORM A SURGICAL PROCEDURE

CROSS-REFERENCE TO RELATED APPLICATION

This Application claims priority from U.S. Provisional Application Nos. 62/526,439, filed Jun. 29, 2017; 62/528,102, filed Jul. 2, 2017; and 62/529,019, filed Jul. 6, 2017. The disclosures of all applications are hereby incorporated herein by reference in their entireties.

FIELD OF THE DISCLOSURE

The present disclosure is generally related to a robotic surgical system in a Virtual Reality (VR) environment.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Robotic surgical devices are now routinely used for numerous surgical procedures such as general surgery, pediatric surgery, and those related to the medical fields of gynecology, urology, cardiology, and otorhinolaryngology. Robotic devices continue to evolve and are being more frequently utilized in surgical procedures.

The robotic devices are used most in surgical procedures that require a high degree of accuracy and/or precision. Such robotic devices include autonomous, tele-operated, and interactive type robotic systems. Interactive robotic systems are most frequently used for providing the surgeon with direct hands-on control of the surgical procedure, thus achieving a high degree of accuracy and/or precision. For example, in a knee surgery, a surgeon can use an interactive robotic arm to sculpt a bone and/or to receive a knee implant. In a laparascopic surgical procedure, using a robotic system, a surgeon may directly control and manipulate tissue, albeit at some distance from the patient through a fulcrum point in the abdominal wall.

In other surgical procedures performed using robotic devices, the surgeon may sit at a console in the operating room, but outside the sterile field, directing and controlling the movements of one or more robotic arms. However, robotic devices can be intrusive during a surgical procedure, blocking the surgeon's point of view and occupying substantial space around an operating table, increasing the likelihood of an operator error.

Instruments for robotic devices, like movement detection equipment and navigation markers, may be implemented in surgical procedures as safeguards. Such instruments help guide the robotic devices and assist the surgeons in avoiding errors. The movement detection equipment and the navigation markers help determine the position of the instrument in space and prevent the instrument from deviating beyond the path set by the surgeon. For example, in neurosurgery, neuromonitors with sensors are used to detect the threshold level, and a signal is sent to an appropriate system to stop insertion of the surgical instrument or to move the instrument away for preventing any damage when an error is detected as being imminent. Further, actuators are also used for controlled movement and positioning of end effectors in the robotic arm.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

Figure 1:
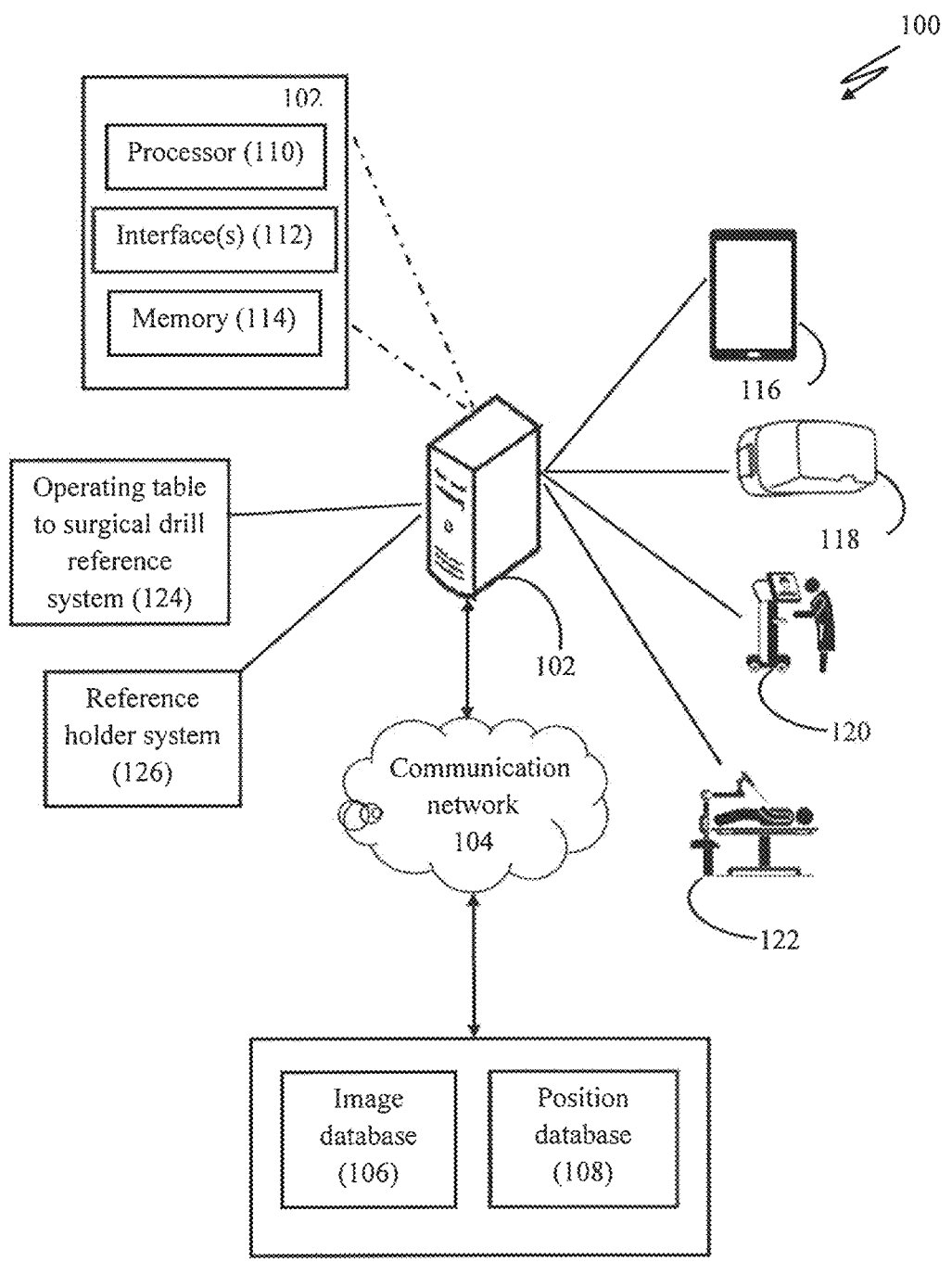
FIG. 1 shows a network connection diagram 100 for a system 102 to guide a robotic surgical system when performing a surgical procedure, according to an embodiment.

FIG. 1 shows a network connection diagram 100 for a system 102 to guide a robotic surgical system when performing surgery, according to an embodiment. The system 102 may be connected to a communication network 104. The communication network 104 may further be connected to an image database 106 and a position database 108 to facilitate data transfer therebetween with the system 102.

The image database 106 may store images of a subject patient, as well as images of previous patients who have undergone similar surgeries. The images may be captured using an X-ray, ultrasound, and Magnetic Resonance Imaging (MRI). Further, the images may be present in raw form, as Three-Dimensional (3D) models, Augmented Reality (AR) images, Virtual Reality (VR) images, and Point of View (PoV) images. The position database 108 may store real mime position information of a PoV surgical drill 122 and that of a virtual drill that may be shown to a surgeon during surgery.

The communication network 104 may be either of a wired and/or a wireless network. The communication network 104, if wireless, may be implemented using communication techniques such as Visible Light Communication (VLC), Worldwide Interoperability for Microwave Access (WIMAX), Long Term Evolution (LTE™), Wireless Local Area Network (WLAN), Infrared (IR) communication, Public Switched Telephone Network (PSTN), Radio waves, and other communication techniques known in the art.

The system 102 may further include a processor 110, interface(s) 112, and a memory 114. The processor 110 may execute an algorithm stored in the memory 114 for processing the PoV images and for guiding the robotic surgical system when performing a surgical procedure. The processor 110 may also be configured to decode and execute any instructions received from one or more other electronic devices or server(s).

In at least one embodiment, the processor 110 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 110 may be configured to execute one or more computer-readable program instructions, such as program instructions to carry out any of the functions described in this description.

The interface(s) 112 may facilitate interaction between a surgeon and the system 102. The interface(s) 112 may accept an input from the surgeon or other user who is associated with an on-going surgery and/or provide an output to the surgeon or other user. The interface(s) 112 may either be a Command Line Interface (CU), Graphical User Interface (GUI), or a voice interface.

The memory 114 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

FIG. 1 also shows a user device 116, AR/VR display 118, guidance drill 120, and a Point of View (PoV) surgical drill 122 that are all connected to the communication network 104. The surgeon may manoeuvre the guidance drill 120 to remotely control the actual PoV surgical drill 122. Locations and motions of the guidance drill 120 may be tracked at all times by an operating table to surgical drill reference system (hereafter "reference system") 124 and a reference holder system 126. The reference holder system 126 and the reference system 124 may control the PoV surgical drill 122 based on the tracked locations and motions thereof.

The user device 116 is shown as a tablet in FIG. 1; however, other user devices having Graphical User Interfaces (GUIs) may also be used. Other implementations of user device 116 may include, but not be limited to, a smart phone, phablet, laptop, and desktop.

FIG. 1 also shows AR/VR display 118 as a VR glass in present case, although the example embodiments are not so limited.

Figure 2:
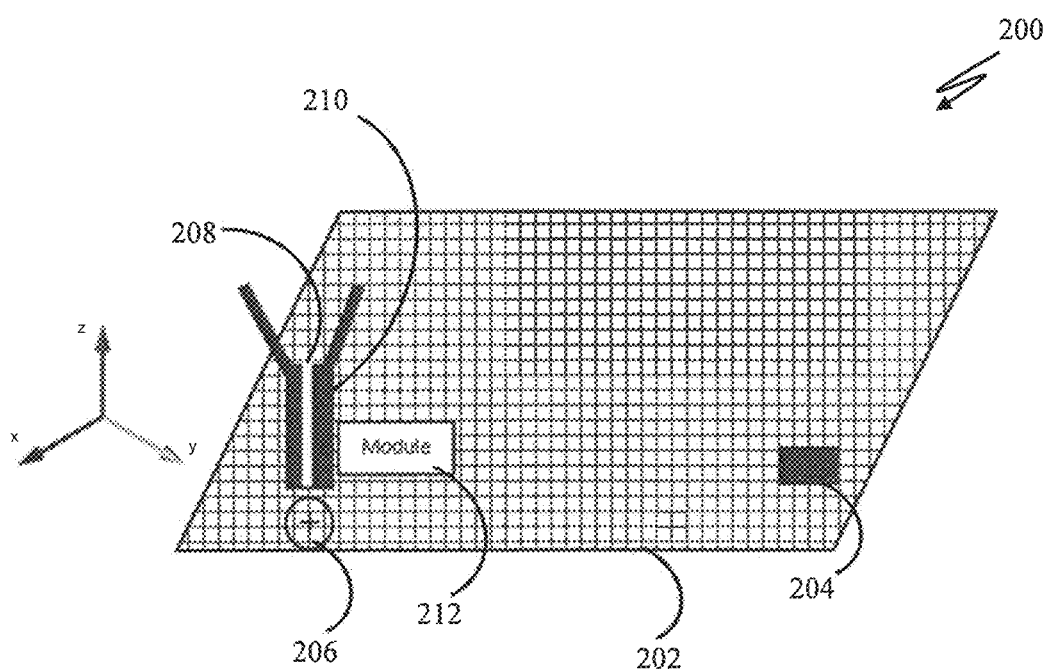
FIG. 2 shows a virtual grid used to determine locations of different instruments present in a Three-Dimensional (3D) space corresponding to an operating table, according to an embodiment.

FIG. 2 shows a virtual grid 200 used to determine locations of different instruments present in a Three-Dimensional (3D) space, by the reference system 124, according to an embodiment. The virtual grid 200 is shown in relation to an operating table 202. A marker 204 for AR reference is used on the virtual grid 200 to help an AR imaging system determine a location of the AR reference. Based on identified location of the AR marker 204, the AR imaging system may identify a location of a drill bit reference 206. Using the location of the drill bit reference 206, the AR/VR display 118 may identify a location of a virtual drill in the 3D space. The virtual drill may be shown to the surgeon, using the AR/VR display 118, during an actual surgical procedure.

In at least one embodiment, a drill bit may be placed in an opening 208 of a drill holder 210 of the PoV surgical drill 122. Once the drill bit is placed in the drill holder 210, a module 212 connected to the drill holder 210 may identify parameters of PoV surgical drill 122, including a type of the surgical drill, a type of the drill bit, a size of the drill bit, and an absolute position of a tip of the drill bit in an XYZ coordinate system referencing the operating table 202.

In at least one embodiment, the module 212 may further comprise a surgical drill reader configured to read a serial number present on the drill bit. The serial number may be related to the PoV surgical drill 122 and/or the drill bit thereof. Serial numbers respectively corresponding to different drill bits and different categories of surgical drills may be stored in a memory corresponding to the module 212. The received serial number may be matched with the serial numbers stored in the memory to identify details related to the PoV surgical drill 122 and the drill bit. In at least one example, the surgical drill reader may be implemented as a Near Field Communication (NFC) reader, and NFC encoded chip may be attached to the drill bit. The NEC reader may therefore communicate with the NFC encoded chip to receive the serial number of the drill bit.

In at least one embodiment, the module 212 may identify and/or determine the drill bit being cradled, reference the position of the drill bit with the virtual grid 200, identify the surgical drill and the drill bit, convert the surgical drill identification to an associated virtual surgical icon, and convert the drill bit identification to an associated virtual surgical drill bit icon. The module 212 may further transmit the virtual surgical icon and the virtual drill bit icon, referenced to the XYZ coordinate system of the operating table 202, to an AR imaging system and to the reference holder system 126.

In at least one other embodiment, the reference holder system 126, shown and described with regard to FIG. 1, may be an integral unit of the PoV surgical drill 122, configured to identify and store, in real-time, XYZ coordinates of the PoV surgical drill 122 and drill bit tip, and an angle of the PoV surgical drill 122. The reference holder system 126 may include an accelerometer to detect changes in position of the PoV surgical drill 122 e.g., a three-axis accelerometer. In at least one other example, the data recorded by the reference holder system 126 may be transmitted to the AR imaging system. The data may include the virtual icon of the PoV surgical drill 122 and the virtual icon of the drill bit along with their real positions relative to the operating table 202.

Figures 3A, 3B:
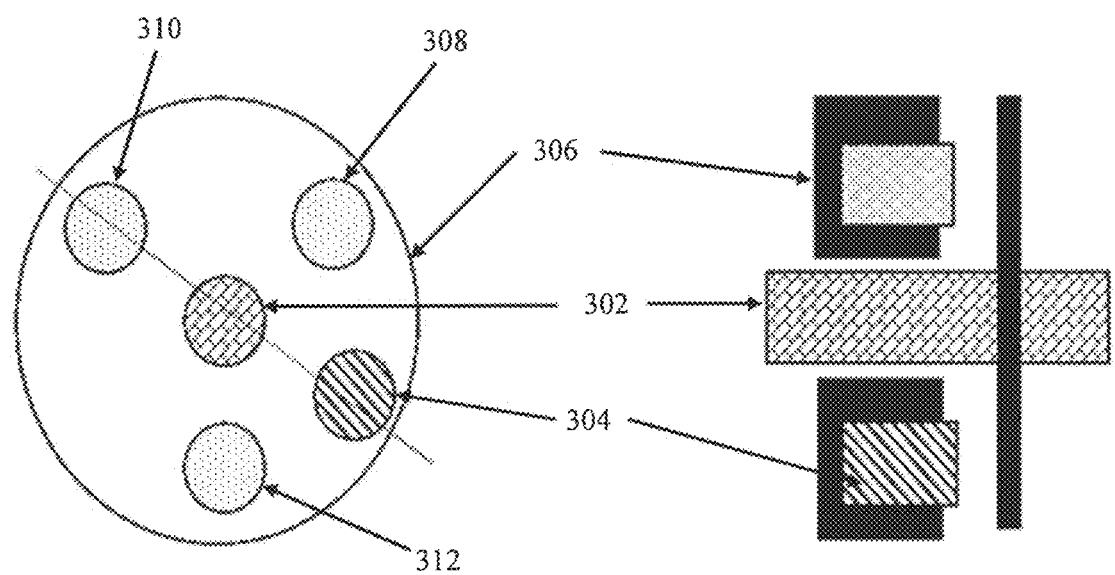
FIG. 3A shows a front point of view (PoV) of a surgical drill, according to an embodiment.
FIG. 3B shows a cross-section PoV of a surgical drill along a Z-Z' axis, according to an embodiment.

FIG. 3A shows a front view of the PoV surgical drill 122; and FIG. 3B shows a cross-section of the PoV surgical drill 122 along a Z-Z' axis, in accordance with at least one example embodiment. Drill bit 302 is centrally located, length-wise, on PoV surgical drill 122. A Light Amplification by Stimulated Emission of Radiation (LASER) device 304 is disposed on the periphery of block 306 surrounding the drill bit 302. The LASER device 304 may guide a surgeon in a direction in which the PoV surgical drill 122 is moving. Further, cameras 308, 310, and 312 are shown on the periphery of the block surrounding the drill bit 302, although the cameras are not so limited in quantity. At least one of the cameras 308, 310, and 312 may capture a PoV image of a surgical area of a subject patient.

In at least one embodiment, images captured by any one or more of the cameras 308, 310, and 312 may be integrated to produce one composite PoV image using known image processing tools and techniques. In at least one example, the composite PoV image may be cropped in a circle and centered with regard to the drill bit 302 based on defaults settings stored by the surgeon. The cropped image may then be sent to the reference holder system 126.

In at least one embodiment, while performing a surgical procedure on the subject patient m the surgeon may maneuver the guidance drill 120 to control the PoV surgical drill 122 based on the PoV images seen on the AR/VR display 118. As set forth above, the PoV images may be collected using one or more of the cameras 308, 310, and 312 positioned on the head of the PoV surgical drill 122. Thus, content of the PoV images may change based on an orientation and direction faced by the PoV surgical drill 122.

In at least one embodiment, the processor 110 may synchronize the position of the PoV surgical drill 122 with a reference linked with augmented images shown on the AR display device 118. Based on such synchronization, a Virtual Reality (VR) drill may be shown to the surgeon on the augmented images displayed using the AR display device 118. The VR drill may move based on changes in position of the PoV surgical drill 122, controlled by the surgeon controlling the guidance drill 120. Thus, such synchronization of the VR drill and the PoV surgical drill 122 provides a realistic experience to the surgeon. Further, operating room cameras may also be used for capturing images of the surgical procedure from a fixed angle, as set by the surgeon or based on a positioning of the operating room cameras. Such images may be stored in the image database 106, and may be displayed to the surgeon using an image display, e.g., AR display device 118.

Figure 4:
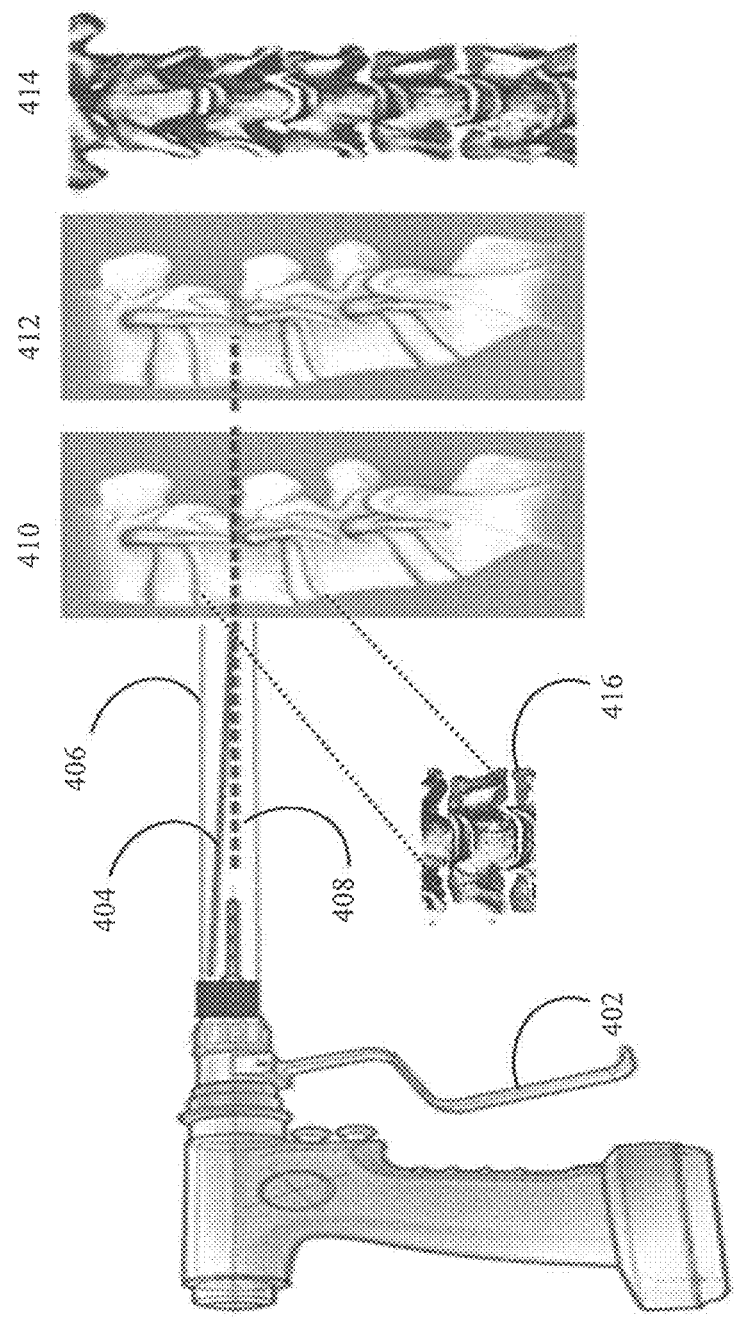
FIG. 4 shows a Virtual Reality (VR) drill set at a first angle, relative to images of the subject patient, according to an embodiment.

FIG. 4 shows the VR drill 402 set at a first angle, relative to images of the subject patient, according to an embodiment. The VR drill 402 is displayed, via a GUI, to the surgeon and other users associated with the surgery; and the VR drill 402 replicates the position and the direction of the PoV surgical drill 122. FIG. 4 also shows a LASER marker 404, a PoV image region 406, and a line of sight 408 of the VR drill 402 (replicating a line of sight of the PoV surgical drill 122). The surgeon may be able to see an actual image 410 of the, e.g., spine of the patient, an AR image 412 of the spine, and a VR image 414 of the spine. The images may be seen based on the surgeon's preferences e.g., images may be overlaid over each other, the images may be shown in parallel in a side to side arrangement, etc. A highlighted section 416 is also shown as the PoV image captured by one or more of the cameras 308, 310, and 312 of the PoV surgical drill 122, in accordance with at least one example.

Figure 5:
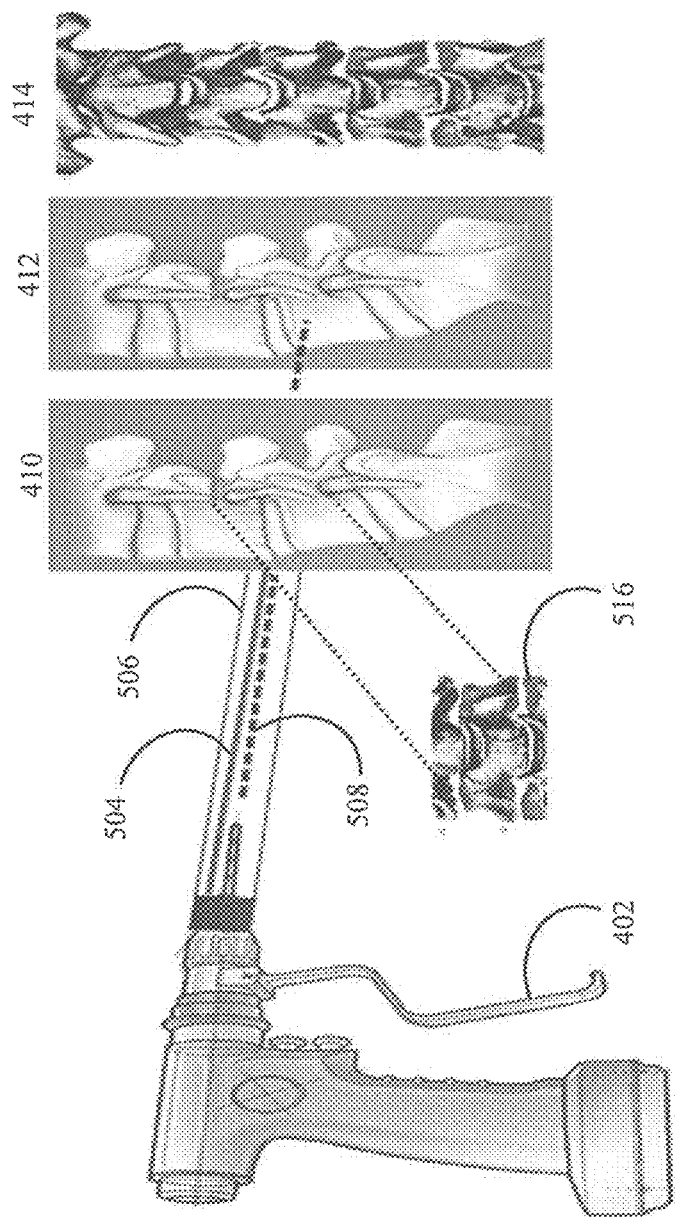
FIG. 5 shows the VR drill set at a second angle relative to the images of the subject patient, according to an embodiment.

FIG. 5 shows the VR drill 402 set at a second angle relative to the images of the subject patient, according to an embodiment. FIG. 5 also shows a LASER marker 504, a PoV image region 506, and a line of sight 508 of the VR drill 402 (replicating a line of sight of the PoV surgical drill 122). The surgeon or other user associated with the surgery may be able to see the actual image 410 of, e.g., the spine of the patient, AR image 412 of the spine, and the VR image 414 of the spine. The images may be seen based on the surgeon's preferences. A highlighted section 516 is also shown as the PoV image captured by at least one of the cameras 308, 310, and 312 of the PoV surgical drill 122, in at accordance with least one example. As evident from comparison of the FIG. 4 and FIG. 5, the position and the direction of the VR drill has changed and thus, content of the PoV images 416 and 516 captured by the cameras of the PoV surgical drill is different. In this way, the surgeon may leverage different points of view to improve accuracy and to reduce errors while performing the surgical procedure.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes shows different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method of guiding a robotic surgical drill, the method comprising:
    displaying a point of view (PoV) image of an affected area of a subject patient, using a plurality of cameras provided around a periphery of a drill bit of the robotic surgical drill, in a digital display, wherein a field of view of the plurality of cameras includes a PoV image region;
    displaying an augmented reality (AR) anatomical image or virtual reality (VR) anatomical image, based on a viewing angle and the PoV image region of the robotic surgical drill;
    guiding the robotic surgical drill, remotely, based on the displayed AR or VR anatomical image using a hand-held guidance drill, the hand-held guidance drill being a same type of drill as the robotic surgical drill, wherein the robotic surgical drill tracks maneuvering of the hand-held guidance drill;
    updating the displayed AR or VR anatomical image based on a change in the viewing angle and the PoV image region of the robotic surgical drill; and
    guiding the robotic surgical drill based on a position and a direction of a virtual version of the robotic surgical drill relative to the updated displayed AR or VR anatomical image.

2. The method of claim 1, wherein the robotic surgical drill is integrated with at least one LASER device.

3. The method of claim 1, wherein the guiding of the robotic surgical drill based on the displayed anatomical image is at least partially manual.

4. The method of claim 1, wherein the guiding of the robotic surgical drill based on the displayed anatomical image is at least partially automatic.

5. The method of claim 1, wherein the robotic surgical drill comprises an end effector attached to a robotic arm.

6. The method of claim 1, wherein a movement of the hand-held guidance drill is tracked by an operating table to a surgical drill reference system and a reference holder system.

7. A non-transitory computer-readable medium having executable instructions stored thereon that, when executed, cause one or more processors to:
    display a point of view (PoV) image of an affected area of a subject patient, using digital images from a plurality of front-facing cameras provided around a periphery of a drill bit of a robotic surgical drill, in a digital display, wherein a field of view of the plurality of cameras includes a PoV image region;
    create references in a Three-Dimensional (3D) space;
    display an augmented reality (AR) anatomical image or a virtual reality (VR) anatomical image, based on a viewing angle and the PoV region of the robotic surgical drill in the 3D space;
    guide the robotic surgical drill, remotely, based on guided movement of a virtual version of the robotic surgical drill on the displayed AR or VR anatomical image from movement of a hand-held guidance drill, the hand-held guidance drill being a same type of tool as the robotic surgical drill, wherein the robotic surgical drill tracks maneuvering of the hand-held guidance drill;

update the displayed AR or VR anatomical image based on a change in the viewing angle and the PoV image region of the robotic surgical drill; and guide the robotic surgical drill based on a position and a direction of a guided movement of the virtual version of the robotic surgical drill on the updated displayed AR or VR anatomical image.

8. The computer-readable medium of claim 7, wherein the robotic surgical drill is integrated with at least one LASER device.

9. The computer-readable medium of claim 7, wherein the guiding of the robotic surgical drill on the displayed anatomical image is at least partially manual.

10. The computer-readable medium of claim 7, wherein the guiding of the robotic surgical drill based on the displayed anatomical image is at least partially automatic.

11. The computer-readable medium of claim 7, wherein the robotic surgical drill comprises an end effector attached to a robotic arm.

12. A system, comprising:
a robotic surgical drill configured to capture a point of view (PoV) image of an affected anatomical area of a subject patient using a plurality of integrated cameras provided around a periphery of a drill bit of the robotic surgical drill, wherein a field of view of the plurality of cameras includes a PoV image region;

a display to display, based on a viewing angle and the PoV image region of the robotic surgical drill, an augmented reality (AR) image or virtual reality (VR) image of the affected anatomical area of the subject patient;

an interface to guide the robotic surgical drill, remotely, based on movement of a virtual version of the robotic surgical drill on the displayed AR or VR image of the affected anatomical area of the subject patient, wherein the interface comprises a hand-held guidance drill, the hand-held guidance drill being a same type of drill as the robotic surgical drill, wherein the robotic surgical drill that is able to be manipulated tracks maneuvering of the hand-held guidance drill; and an image database to store and update the AR or VR image of the affected anatomical area of the subject patient, wherein the interface updates guidance for the robotic surgical drill based on updates to the AR or VR image of the affected anatomical area of the subject patient retrieved from the image database.

13. The system of claim 12, wherein the robotic surgical drill is integrated with at least a LASER device.

14. The system of claim 12, wherein the guiding of the robotic surgical drill based on the displayed image of the affected anatomical area is at least partially manual.

15. The system of claim 12, wherein the guiding of the robotic surgical drill based on the displayed image of the affected anatomical area is at least partially automatic.

* * * * *